(12) United States Patent
Long et al.

(10) Patent No.: US 10,702,207 B2
(45) Date of Patent: Jul. 7, 2020

(54) SYSTEM AND METHOD FOR DETERMINING SPECTRAL BOUNDARIES FOR SLEEP STAGE CLASSIFICATION

(71) Applicant: KONINKLIJKE PHILIPS N.V., Eindhoven (NL)

(72) Inventors: Xi Long, Eindhoven (NL); Reinder Haakma, Eindhoven (NL); Pedro Miguel Ferreira Dos Santos Da Fonseca, Borgerhout (BE); Ronaldus Maria Aarts, Geldrop (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 292 days.

(21) Appl. No.: 15/533,084

(22) PCT Filed: Dec. 4, 2015

(86) PCT No.: PCT/IB2015/059341
§ 371 (c)(1),
(2) Date: Jun. 5, 2017

(87) PCT Pub. No.: WO2016/092433
PCT Pub. Date: Jun. 16, 2016

(65) Prior Publication Data
US 2017/0360361 A1     Dec. 21, 2017

Related U.S. Application Data

(60) Provisional application No. 62/090,534, filed on Dec. 11, 2014.

(51) Int. Cl.
*A61B 5/00* (2006.01)
*A61B 5/024* (2006.01)
(Continued)

(52) U.S. Cl.
CPC ........ *A61B 5/4812* (2013.01); *A61B 5/02438* (2013.01); *A61B 5/0402* (2013.01);
(Continued)

(58) Field of Classification Search
CPC ... A61B 5/0816; A61B 5/1118; A61B 5/1135; A61B 5/4812; A61B 5/7257;
(Continued)

(56) References Cited

U.S. PATENT DOCUMENTS 7,623,912 B2 * 11/2009 Akselrod ........... A61B 5/02405
600/513
7,860,561 B1 * 12/2010 Modarres ............. A61B 5/0476
600/544
(Continued)

FOREIGN PATENT DOCUMENTS

| CN | 103211598 A | 7/2013 |
| EP | 2286723 A1 | 2/2011 |
| WO | 2004107978 A1 | 12/2004 |

OTHER PUBLICATIONS

Cysarz, D., Zerm, R., Bettermann, H., Frühwirth, M., Moser, M., & Kröz, M. (2008). Comparison of respiratory rates derived from heart rate variability, ECG amplitude, and nasal/oral airflow. Annals of biomedical engineering, 36(12), 2085-2094. (Year: 2008).*
(Continued)

*Primary Examiner* — Max F Hindenburg

(57) ABSTRACT

The present disclosure pertains to a system (10) configured to determine spectral boundaries (216, 218) for sleep stage classification in a subject (12). The spectral boundaries may be customized and used for sleep stage classification in an individual subject. Spectral boundaries determined by the system that are customized for the subject may facilitate sleep stage classification with higher accuracy relative to classifications made based on static, fixed spectral boundaries that are not unique to the subject. In some implemen-
(Continued)

tations, the system comprises one or more of a sensor (16), a processor (20), electronic storage (22), a user interface (24), and/or other components.

10 Claims, 4 Drawing Sheets

(51) Int. Cl.
*A61B 5/08* (2006.01)
*A61B 5/0402* (2006.01)
*A61B 5/11* (2006.01)
*A61B 5/113* (2006.01)

(52) U.S. Cl.
CPC .............. *A61B 5/0816* (2013.01); *A61B 5/11* (2013.01); *A61B 5/681* (2013.01); *A61B 5/7257* (2013.01); *A61B 5/02416* (2013.01); *A61B 5/1118* (2013.01); *A61B 5/1135* (2013.01)

(58) Field of Classification Search
CPC . A61B 5/0418; A61B 5/02438; A61B 5/0402; A61B 5/681
See application file for complete search history.

(56) References Cited

U.S. PATENT DOCUMENTS

| | | | |
|---|---|---|---|
| 9,820,698 B2* | 11/2017 | Fonseca | A61B 5/1135 |
| 2007/0016095 A1* | 1/2007 | Low | A61B 5/048 600/544 |
| 2009/0131803 A1* | 5/2009 | Heneghan | A61B 5/4812 600/484 |
| 2010/0217146 A1* | 8/2010 | Osvath | A61B 5/0478 600/544 |
| 2011/0034811 A1 | 2/2011 | Naujokat et al. | |
| 2012/0125337 A1 | 5/2012 | Asanoi | |
| 2014/0275852 A1* | 9/2014 | Hong | A61B 5/02427 600/301 |
| 2015/0313535 A1* | 11/2015 | Alshaer | A61B 5/4812 600/529 |
| 2016/0324465 A1* | 11/2016 | Osvath | A61B 5/0488 |

OTHER PUBLICATIONS

Kantelhardt, J. W., Penzel, T., Rostig, S., Becker, H. F., Havlin, S., & Bunde, A. (2003). Breathing during REM and non-REM sleep: correlated versus uncorrelated behaviour. Physica A: Statistical Mechanics and its Applications, 319, 447-457. (Year: 2003).*

Karlen, W., Mattiussi, C., & Floreano, D. (2009). Sleep and wake classification with ECG and respiratory effort signals. IEEE Transactions on Biomedical Circuits and Systems, 3(2), 71-78. (Year: 2009).*

Penzel, T., Wessel, N., Riedl, M., Kantelhardt, J. W., Rostig, S., Glos, M., . . . & Fietze, I. (2007). Cardiovascular and respiratory dynamics during normal and pathological sleep. Chaos: An Interdisciplinary Journal of Nonlinear Science, 17(1), 015116. (Year: 2007).*

Redmond, S. J., & Heneghan, C. (2006). Cardiorespiratory-based sleep staging in subjects with obstructive sleep apnea. IEEE Transactions on Biomedical Engineering, 53(3), 485-496. (Year: 2006).*

Redmond, S. J., de Chazal, P., O'Brien, C., Ryan, S., McNicholas, W. T., & Heneghan, C. (2007). Sleep staging using cardiorespiratory signals. Somnologie-Schlafforschung und Schlafmedizin, 11(4), 245-256. (Year: 2007).*

Sloboda, J., & Das, M. (Jul. 2011). A simple sleep stage identification technique for incorporation in inexpensive electronic sleep screening devices. In Proceedings of the 2011 IEEE National Aerospace and Electronics Conference (NAECON) (pp. 21-24). IEEE. (Year: 2011).*

Xi Long et al: "Spectral Boundary Adaptation on Heart Rate Variability for Sleep and Wake Classification", International Journal of Artificial Intelligence Tools, vol. 23, No. 3, May 28, 2014 (May 28, 2014), p. 1460002, XP055250219, SG ISSN: 0218-2130. DOI: 10.1142/S0218213014600021, sections 2.1 to 2.6.

Long Xi et al: "Improving sleep/wake detection via boundary adaptation for respiratory spectral features", 2015 37th Annual International Conference of the IEEE Engineering in Medicine and Biology Society (EMBC), IEEE, Aug. 25, 2015, pp. 374-377, sections 2A to 2E, figure 1.

A. Rechtschaffen and A. Kales, Eds., A manual of standardized terminology, techniques and scoring system for sleep stages of human subjects, National Institutes of Health, Washington, DC, 1968.

S. J. Redmond, et al., "Sleep staging using cardiorespiratory signals," Somnologie, vol. 11, pp. 245-256, 2007.

S. Devot, D. Dratwa, and E. Naujokat, "Sleep/wake detection based on cardiorespiratory signals and actigraphy," in Proc. 32nd Ann. Int. Conf. IEEE Eng. Med. Biol. Soc., Buenos Aires, Argentina, Aug. 2010, pp. 5089-5092.

X. Long, P. Fonseca, R. Haakma, J. Foussier, and R. M. Aarts, "Sleep and wake classification with actigraphy and respiratory effort using dynamic warping," IEEE J. Biomed. Health Inf., Accepted for publication, 2014.

* cited by examiner

SYSTEM AND METHOD FOR DETERMINING SPECTRAL BOUNDARIES FOR SLEEP STAGE CLASSIFICATION

CROSS-REFERENCE TO PRIOR APPLICATIONS

This application is the U.S. National Phase application under 35 U.S.C. § 371 of International Application Serial No. PCT/IB2015/059341, filed on 4 Dec. 2015, which claims the benefit of U.S. Provisional Ser. No. 62/090,534, filed on 11 Dec. 2014. These applications are hereby incorporated by reference herein.

BACKGROUND

1. Field

The present disclosure pertains to a system and method for determining spectral boundaries for sleep stage classification.

2. Description of the Related Art

Assessment of sleep quality based on monitoring sleep and wake phases during bedtime is known. Over-night polysomnography (PSG) recordings with manually scored hypnograms (done by sleep technicians) for analysis of sleep architecture and occurrence of specific sleep-related problems is known. The analysis is performed based on fixed spectral boundaries that are not individually adjusted for a particular subject.

SUMMARY

Accordingly, one or more aspects of the present disclosure relate to a system configured to determine spectral boundaries for sleep stage classification in a subject. The system comprises one or more sensors, one or more physical computer processors, and/or other components. The one or more sensors are configured to generate output signals that convey information related to a respiratory wave amplitude metric for a sleep session of the subject. The one or more physical computer processors are configured by computer readable instructions to transform the information conveyed by the output signals in individual epochs of time into a frequency domain; determine individual frequencies of respiratory wave amplitude metric peaks within the individual epochs of time; determine an aggregated frequency of the respiratory wave amplitude metric peaks by aggregating the individual frequencies of the respiratory wave metric peaks within the individual epochs of time; determine the spectral boundaries for sleep stage classification for the subject based on the aggregated frequency; and determine sleep stages of the subject during individual epochs of time in a subsequent sleep session as a function of the aggregated frequency of respiratory wave amplitude metric peaks using the determined spectral boundaries.

Another aspect of the present disclosure relates to a method to determine spectral boundaries for sleep stage classification in a subject with a determination system. The determination system comprises one or more sensors, one or more physical computer processors, and/or other components. The method comprises generating, with the one or more sensors, output signals that convey information related to a respiratory wave amplitude metric for a sleep session of the subject; transforming, with the one or more physical computer processors, the information conveyed by the output signals in individual epochs of time into a frequency domain; determining, with the one or more physical computer processors, individual frequencies of respiratory wave amplitude metric peaks within the individual epochs of time; determining, with the one or more physical computer processors, an aggregated frequency of the respiratory wave amplitude metric peaks by aggregating the individual frequencies of the respiratory wave metric peaks within the individual epochs of time; determining, with the one or more physical computer processors, the spectral boundaries for sleep stage classification for the subject based on the aggregated frequency; and determining, with the one or more physical computer processors, sleep stages of the subject during individual epochs of time in a subsequent sleep session as a function of the aggregated frequency of respiratory wave amplitude metric peaks using the determined spectral boundaries.

Still another aspect of the present disclosure relates to a system configured to determine spectral boundaries for sleep stage classification in a subject. The system comprises means for generating output signals that convey information related to a respiratory wave amplitude metric for a sleep session of the subject; means for transforming the information conveyed by the output signals in individual epochs of time into a frequency domain; means for determining individual frequencies of respiratory wave amplitude metric peaks within the individual epochs of time; means for determining an aggregated frequency of the respiratory wave amplitude metric peaks by aggregating the individual frequencies of the respiratory wave metric peaks within the individual epochs of time; means for determining the spectral boundaries for sleep stage classification for the subject based on the aggregated frequency; and means for determining sleep stages of the subject during individual epochs of time in a subsequent sleep session as a function of the aggregated frequency of respiratory wave amplitude metric peaks using the determined spectral boundaries.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
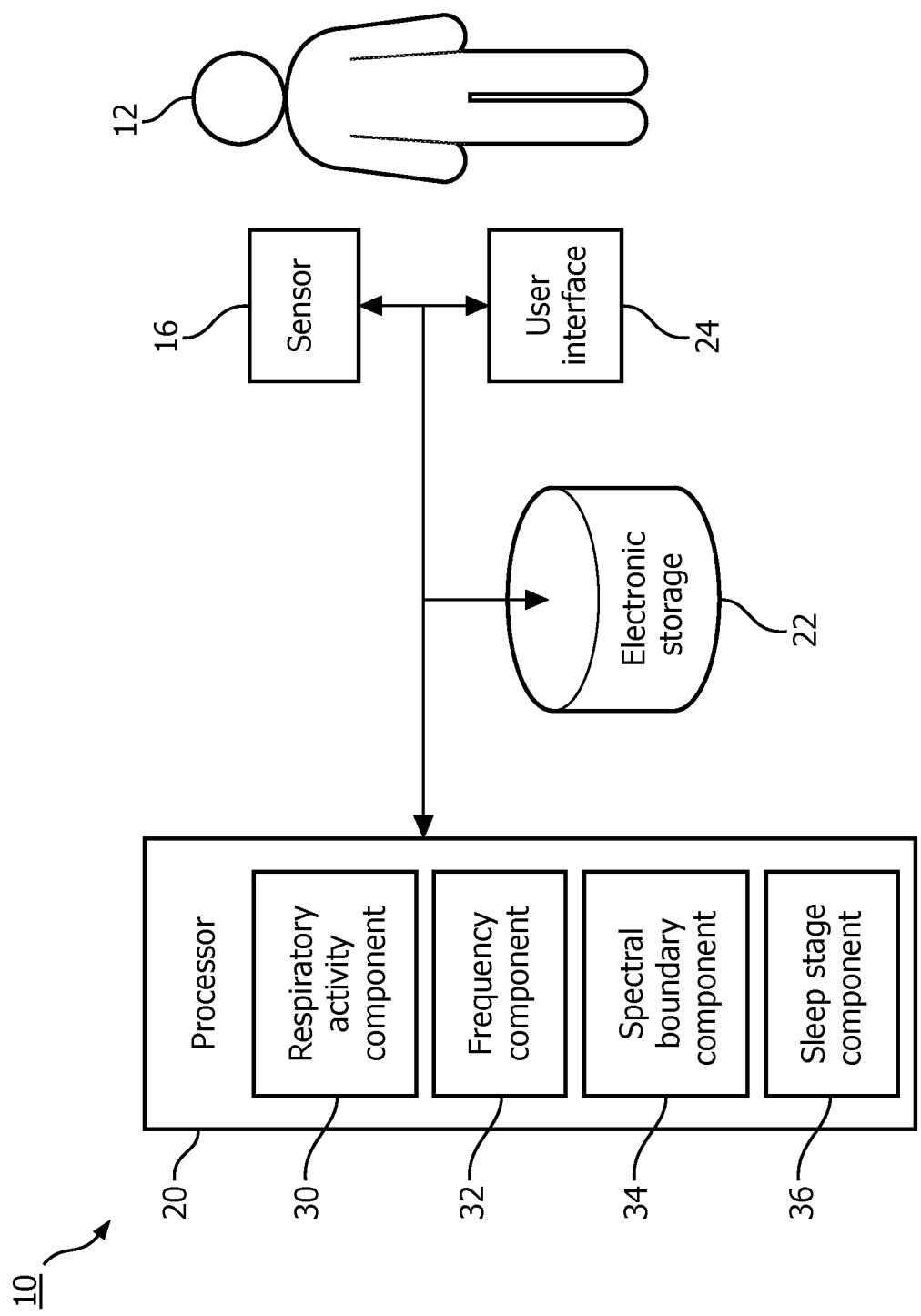
FIG. 1 illustrates a system configured to determine spectral boundaries for sleep stage classification in a subject.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 illustrates a system 10 configured to determine spectral boundaries for sleep stage classification in a subject 12. The spectral boundaries and/or other information related to respiratory activity in subject 12 may be used for sleep stage classification. This is because respiratory activity is associated with autonomic nervous activity (ANA) and breathing control which vary during sleep and wakefulness. The information related to respiratory activity that is used for sleep stage classification may be determined based on a spectral analysis (e.g., using the spectral boundaries) of respiratory effort by subject 12, for example. The spectral analysis may include determining and/or otherwise analyzing spectral powers in different frequency bands (bounded by the determined spectral boundaries) including a very low frequency (VLF) band, a low frequency (LF) band, and a high frequency (HF) band, of respiratory signals from subject 12, and/or other analysis. Spectral boundaries determined by system 10 that are customized for subject 12 may facilitate sleep stage classification with higher accuracy relative to classifications made based on static, fixed spectral boundaries that are not unique to subject 12. In some implementations, system 10 comprises one or more of a sensor 16, a processor 20, electronic storage 22, a user interface 24, and/or other components.

Sensor 16 is configured to generate output signals conveying information related to respiratory activity in subject 12, cardiac activity in subject 12, movement of subject 12, and/or other information. The respiratory activity, cardiac activity, and/or movement of subject 12 may correspond to a respiratory effort of subject 12 and/or other characteristics of subject 12. The respiratory activity, cardiac activity, and/or movement of subject 12 may correspond to a sleep stage of subject 12 and/or other characteristics of subject 12. The sleep stage of subject 12 may be associated with rapid eye movement (REM) sleep, non-rapid eye movement (NREM) sleep, and/or other sleep. Sensor 16 may comprise one or more sensors that measure such parameters directly and/or indirectly. For example, one or more sensors 16 may generate an output based on a heart rate of subject 12 (e.g., sensor 16 may be a heart rate sensor located on the chest of subject 12, and/or be configured as a bracelet on a wrist of subject 12, and/or be located on another limb of subject 12), movement of subject 12 (e.g., sensor 16 may include a bracelet around the wrist and/or ankle of subject 12 with an accelerometer such that sleep may be analyzed using actigraphy signals), respiration of subject 12, and/or other characteristics of subject 12. In some embodiments, respiratory signals may be measured directly, for example with a chest belt and/or a nose cannula, and/or may be derived from other signals such as photoplethysmography (PPG) signals and/or heart rate, which can be easily be measured, for example, with a wrist-worn sensor device. Although sensor 16 is illustrated at a single location near subject 12, this is not intended to be limiting. Sensor 16 may include sensors disposed in a plurality of locations, such as for example, within (or in communication with) user interface 24, coupled (in a removable manner) with clothing of subject 12, worn by subject 12 (e.g., as a headband, wristband, etc.), positioned to point at subject 12 while subject 12 sleeps (e.g., a camera that conveys output signals related to movement of subject 12), and/or in other locations.

In some embodiments, sensor 16 is configured to generate output signals conveying information related to an amplitude and/or power of cardiac, respiratory, movement, and/or other (e.g., respiratory effort) signals from subject 12. The output signals may fluctuate with cardiac, respiratory, and/or movement signal wave amplitudes and/or powers as a function of time. In some embodiments, sensor 16 is configured to generate output signals that convey information related to a specific cardiac, respiratory, and/or movement wave amplitude metric for a sleep session of subject 12. This specific cardiac, respiratory, and/or movement wave amplitude metric may be and/or include a power spectral density and/or other metrics of the cardiac, respiratory, movement, and/or other (e.g., respiratory effort) signals from subject 12, for example.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device, or processor 20 may represent processing functionality of a plurality of devices operating in coordination.

As shown in FIG. 1, processor 20 is configured to execute one or more computer program components. The one or more computer program components may comprise one or more of a respiratory activity component 30, a frequency component 32, a spectral boundary component 34, a sleep stage component 36, and/or other components. Processor 20 may be configured to execute components 30, 32, 34, and/or 36 by software; hardware; firmware; some combination of software, hardware, and/or firmware; and/or other mechanisms for configuring processing capabilities on processor 20.

It should be appreciated that although components 30, 32, 34, and 36 are illustrated in FIG. 1 as being co-located within a single processing unit, in embodiments in which processor 20 comprises multiple processing units, one or more of components 30, 32, 34, and/or 36 may be located remotely from the other components. The description of the functionality provided by the different components 30, 32, 34, and/or 36 described below is for illustrative purposes, and is not intended to be limiting, as any of components 30, 32, 34, and/or 36 may provide more or less functionality than is described. For example, one or more of components 30, 32, 34, and/or 36 may be eliminated, and some or all of its functionality may be provided by other components 30, 32, 34, and/or 36. As another example, processor 20 may be configured to execute one or more additional components that may perform some or all of the functionality attributed below to one of components 30, 32, 34, and/or 36.

In some embodiments, respiratory activity component 30 is configured to facilitate low pass filtering (e.g., a $10^{th}$ order Butterworth filter with a cut-off frequency of about 0.7 Hz) and then normalization (e.g., by subtracting a median peak-trough amplitude estimated over an entire sleep session to remove a signal baseline) of the output signals (e.g., respiratory effort signals) from sensors 16. Then, respiratory activity component 30 is configured to transform the information conveyed by the filtered and/or normalized output signals into a frequency domain. Respiratory activity component 30 is configured to separate the output signals into signal segments that correspond to individual time epochs of information. The length of the individual time epochs may be determined by respiratory activity component 30, may be determined at manufacture, and/or may be determined by other methods. In some embodiments, an individual time epoch may be about 30 seconds long. In some embodiments, respiratory activity component 30 is configured to transform the output signals (or some derivation thereof) into a frequency domain epoch by epoch to create transformed signal segments. In some embodiments, creating the transformed signal segments may include performing a Fourier Transform, a Fast Fourier Transform, or some other transform on segments of the output signal (or derivation thereof) that correspond to the individual epochs of time.

In some embodiments, respiratory activity component 30 is configured to determine one or more respiratory (effort) wave amplitude metrics based on the transformed signal segments. Respiratory (effort, e.g., and/or cardiac and/or movement) wave amplitudes may be indicative of respiratory wave power. In some embodiments, respiratory activity component 30 is configured to determine a respiratory wave amplitude metric such as power spectral density and/or other metrics. Power spectral density describes how the strength of a respiratory wave signal is distributed in a frequency domain. Power spectral density describes power contributed to a wave, by a frequency, per unit frequency. Power spectral density describes a rate of variance in characteristics of a wave as a function of frequency. An integral of the power spectral density over a given frequency band gives an average power in a signal over that frequency band, for example. In some embodiments, respiratory activity component 30 is configured to determine a respiratory wave amplitude metric such as power spectral density, average power spectral density, average normalized power spectral density, and/or other metrics. Such determinations may be made for individual time epochs that correspond to the individual transformed signal segments (e.g., on a per-segment basis).

In some embodiments, within individual transformed (respiratory effort) signal segments, the logarithms of spectral powers within the VLF, the LF, and the HF bands may be determined by respiratory activity component 30 as well as a ratio of LF and HF band spectral powers, and/or other information. The power spectral density of the individual bands may be normalized by dividing the power spectral density of an individual band by the total spectral power in the LF and HF bands. In some embodiments, respiratory activity component 30 is configured to transform 30 second power spectral density epochs into the frequency domain, normalize the 30 second power spectral density epochs, average the normalized 30 second power spectral density epochs, and/or analyze the output signals in other ways.

Figure 2:
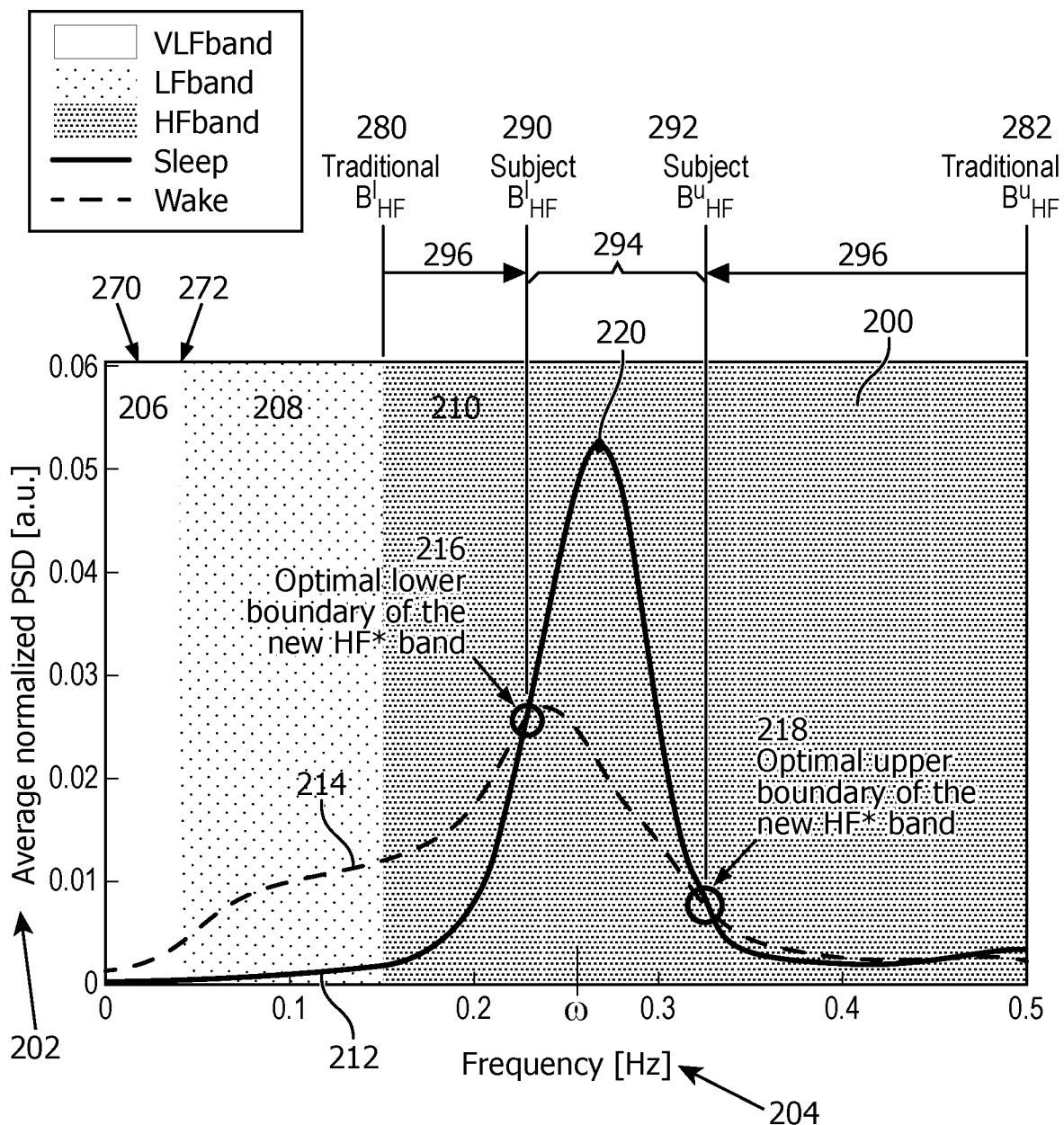
FIG. 2 illustrates a plot of average normalized power spectral density as a function of frequency.

By way of a non-limiting example, FIG. 2 illustrates a plot 200 of average normalized power spectral density 202 as a function of frequency 204 (e.g., in the frequency domain) for an individual 30 second (for example) epoch (e.g., an individual transformed signal segment). FIG. 2 illustrates the VLF band 206, the LF band 208, and the HF band 210 at traditional fixed boundary positions (e.g., VLF is typically considered to be 0.01-0.05 Hz, LF is typically considered to be 0.05-0.15 Hz, and HF is typically considered to be 0.15-0.5 Hz). FIG. 2 illustrates the normalized power spectral density of a sleep epoch 212 and a wake epoch 214. As described below, spectral boundaries determined for subject 12 correspond to locations 216, 218 where the average normalized power spectral density of wake epoch 214 and sleep epoch 212 cross over each other. The frequencies that correspond to locations 216 and 218 determined for subject 12 are not the same as the traditional fixed boundary frequencies of the HF band (thus determining sleep stages based on spectral boundaries that correspond to locations 216 and 218, instead of the traditional fixed boundary frequencies of the HF band, will produce more accurate sleep stage determinations for subject 12).

Frequency component 32 (FIG. 1) is configured to determine individual frequencies of respiratory (effort) wave amplitude metric peaks (e.g., average normalized power spectral density peaks) within the individual epochs of time (e.g., within individual transformed signal segments). For example, in FIG. 2, frequency component 32 is configured to determine the frequency of peak 220 (e.g., about 0.26 Hz) for the 30 second (for example) epoch of the transformed signal segment shown in FIG. 2. Frequency component 32 is configured to determine an aggregated frequency of the respiratory wave amplitude metric peaks by aggregating the individual frequencies of the respiratory wave metric peaks (e.g., peaks 220) within the individual epochs of time (e.g., multiple similar epochs/transformed signal segments to the one shown in FIG. 2). As used herein, an aggregated peak frequency refers to a value for frequency determined from consideration and/or combination of the peak frequency values of the respiratory wave amplitude metric of multiple transformed signal segments. For example, the aggregated peak frequency may be determined through one or more of averaging peak frequencies of the multiple transformed signal elements, a summation of one or more characteristics of the multiple transformed signal elements, graphically overlaying multiple transformed signal elements and visually and/or graphically determining a peak frequency, and/or other methods. In some embodiments, determining the aggregated frequency of the respiratory wave amplitude metric peaks comprises averaging frequencies of average normalized power spectral density peaks (e.g., peak 220 in FIG. 2) from the individual epochs of time. In some embodiments, an average frequency of the power spectral density peaks from individual thirty second epochs of time during the sleep session is a mean respiratory frequency, ω, of subject 12 for a sleep session. In some embodiments, frequency component 32 (FIG. 1) is configured to determine power spectral density peaks (e.g., peaks 220) only within the traditional LF and HF bands (e.g., 0.01-0.5 Hz) because the respiration frequency of healthy people typically lies with this range.

Spectral boundary component 34 (FIG. 1) is configured to determine spectral boundaries (e.g., that correspond to the frequencies of locations 216 and 218 in FIG. 2) in subject 12. The spectral boundaries may correspond to different levels of alertness (e.g., different sleep stages) in subject 12. For example, the spectral boundaries may define, describe, and/or be related to sleep stages such as light REM sleep, deep NREM sleep, and/or other sleep stages.

The spectral boundaries (B) are determined based on the aggregated frequency (ω) determined by frequency component 32, and/or other information. In some embodiments, spectral boundary component 34 (FIG. 1) is configured to determine upper ($B^u_{HF}$) and lower ($B^l_{HF}$) spectral boundaries 290, 292 of the HF band (e.g., corresponding to frequencies of locations 218 and 216 in FIG. 2) of subject 12 (FIG. 1). The lower spectral boundary 290 of the HF band may be the same as the upper spectral boundary of the LF band ($B^u_{LF}$). Spectral boundary component 34 is configured such that the upper and lower boundaries 270, 272 of the VLF band remain fixed at 0.01-0.05 Hz (which means that the lower boundary of the LF band, $B^l_{LF}$, is also 0.05 Hz). In some embodiments, the upper ($B^u_{HF}$) and lower ($B^l_{HF}$) spectral boundaries of the HF band are determined for subject 12 based on the aggregated (respiratory) frequency ω of subject 12 using linear regression and regression coefficients according to the equation:

$$B = a\omega + b$$

where B is an individual boundary for a subject 12 (e.g., $B=B^u_{HF}$ or $B=B^l_{HF}$), ω is the aggregated (mean respiratory) frequency determined by frequency component 32, and a and b are regression coefficients (e.g., slope and intercept). Regression coefficients a and b may include upper regression coefficients $a^u$ and $b^u$ used when determining $B^u_{HF}$ and lower regression coefficients $a^l$ and $b^l$ used when determining $B^l_{HF}$. By way of a non-limiting example, the equation $B^u_{HF} = a^u\omega + b^u$ may be used to determine the upper boundary of the HF band in subject 12 and the equation $B^l_{HF} = a^l\omega + b^l$ may be used to determine the lower boundary of the HF band in subject 12.

The regression coefficients a and b are determined by spectral boundary component 34 based on sleep information obtained from a population of users. The two regression coefficients a and b are determined using one or more methods such as the least square estimation (LSE) method, maximum likelihood estimation (MSE), and/or other methods, based on the equations:

$$a = \frac{n\sum_{i=1}^{n}\omega_i B_i - \left(\sum_{i=1}^{n}\omega_i \sum_{i=1}^{n}B_i\right)}{n\sum_{i=1}^{n}\omega_i^2 - \left(\sum_{i=1}^{n}\omega_i\right)^2}$$

$$b = \frac{1}{n}\left(\sum_{i=1}^{n}B_i - a\sum_{i=1}^{n}\omega_i\right)$$

where $B_i = \{B_1, B_2, \ldots, B_i, \ldots, B_n\}$ (i=1, 2, . . . , n) is a set of previously determined boundaries from n different subjects in a population of subjects, and $\omega = \{\omega_1, \omega_2, \ldots, \omega_i, \ldots, \omega_n\}$ (i=1, 2, . . . , n) are the corresponding previously determined mean respiratory frequencies from n subjects (e.g., determined as described above for subject 12 for the individual subjects in the population). By way of a non-limiting example, upper regression coefficients $a^u$ and $b^u$ may be determined based on upper boundaries (e.g., $B^u_{HF}$) previously determined for the individual subjects in the population of subjects and lower regression coefficients $a^l$ and $b^l$ may be determined based on lower boundaries (e.g., $B^l_{HF}$) previously determined for the individual subjects in the population of subjects. In some embodiments, the previously determined information for the population of subjects may be programmed at manufacture of system 10, stored in electronic storage 22 and/or in other locations and obtained by spectral boundary component 34, entered and/or selected (e.g., by subject 12, a doctor, a caregiver, and/or other users) via user interface 24, and/or determined in other ways.

Sleep stage component 36 (FIG. 1) is configured to determine sleep stages of subject 12. The sleep stages are determined for individual epochs of time in a subsequent sleep session as a function of the aggregated frequency of respiratory wave amplitude metric peaks (ω) using the determined spectral boundaries ($B^u_{HF}$ and $B^l_{HF}$). In some embodiments, sleep stage component 34 is configured to determine sleep stages based on the output signals from sensors 16, the determined spectral boundaries, and/or other information. For example, FIG. 2 illustrates traditional upper and lower HF band spectral boundaries 280 and 282 and newly determined upper and lower HF band spectral boundaries 290 and 292 determined specifically for subject 12 (FIG. 1). The subject 12 HF band 294 is narrower 296 than the traditional HF band 210. Determining sleep stages based on spectral boundaries that correspond to locations upper and lower boundaries 290 and 292, instead of the traditional fixed upper and lower boundaries 280 and 282 will produce more accurate sleep stage determinations for subject 12.

Figure 3:
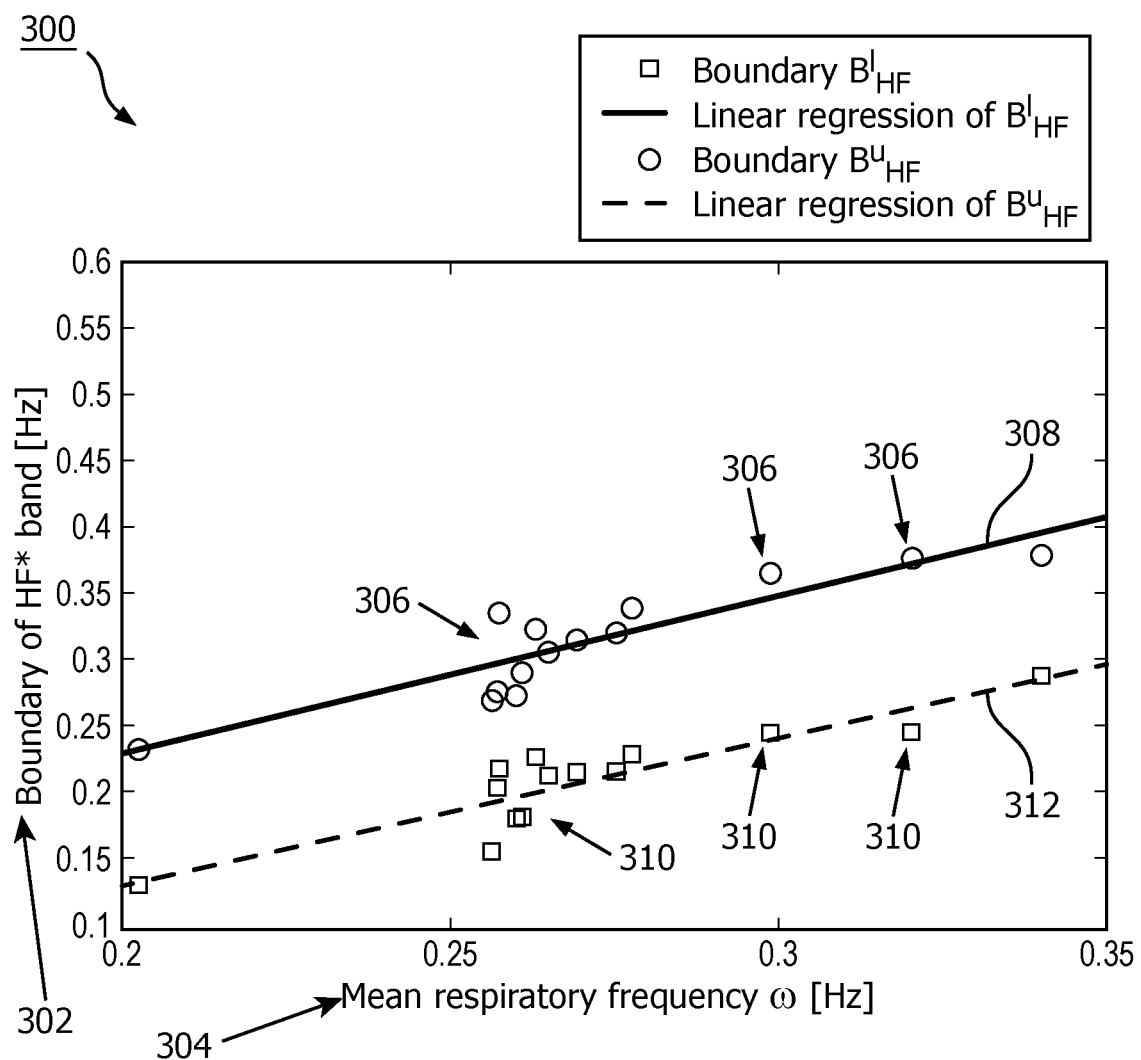
FIG. 3 illustrates an example of spectral boundaries of a high frequency band determined for an individual subject using a linear regression model.

FIG. 3 illustrates an example of spectral boundaries of the HF band determined for an individual subject 12 using the linear regression model described above. FIG. 3 illustrates that boundaries for an individual subject 12 may be linearly estimated based on the aggregated (mean respiratory) frequency ω. FIG. 3 is a plot 300 of determined boundary frequency 302 versus mean respiratory frequency 304. FIG. 3 shows upper HF band boundary determinations 306 as a function of ω in subject 12 and a corresponding linear regression 308, as well as determined lower HF band boundary determinations 310 as a function of ω in subject 12 and a corresponding linear regression 312.

Returning to FIG. 1, electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 22 may store software algorithms, information determined by processor 20, information received via user interface 24 and/or external computing systems, and/or other information that enables system 10 to function properly. Electronic storage 22 may be (in whole or in part) a separate component within system 10, or electronic storage 22 may be provided (in whole or in part) integrally with one or more other components of system 10 (e.g., processor 20).

User interface 24 is configured to provide an interface between system 10 and subject 12, and/or other users through which subject 12 and/or other users may provide information to and receive information from system 10. This enables data, cues, results, and/or instructions and any other communicable items, collectively referred to as "information," to be communicated between a user (e.g., subject 12) and one or more of sensor 16, processor 20, and/or other components of system 10. For example, adjusted spectral boundaries may be displayed to a caregiver via user interface 24.

Examples of interface devices suitable for inclusion in user interface 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 24 comprises a plurality of separate interfaces. In some embodiments, user interface 24 comprises at least one interface that is provided integrally with processor 20 and/or other components of system 10.

It is to be understood that other communication techniques, either hard-wired or wireless, are also contemplated by the present disclosure as user interface 24. For example, the present disclosure contemplates that user interface 24 may be integrated with a removable storage interface provided by electronic storage 22. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 24 comprise, but are not limited to, an RS-232 port, RF link, an IR link, modem (telephone, cable or other). In short, any technique for communicating information with system 10 is contemplated by the present disclosure as user interface 24.

Figure 4:
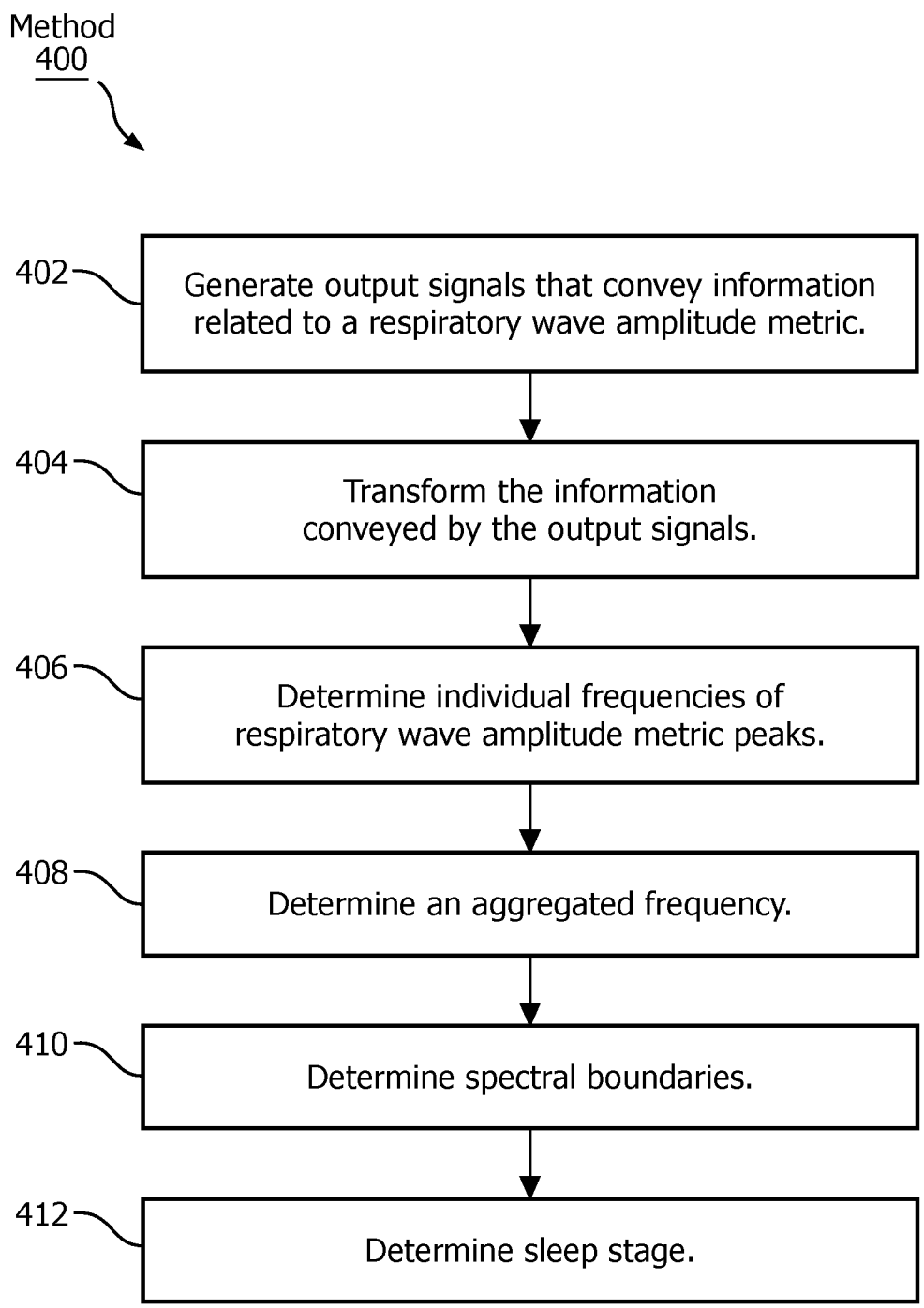
FIG. 4 illustrates a method to determine spectral boundaries for sleep stage classification in a subject with a determination system.

FIG. 4 illustrates a method 400 to determine spectral boundaries for sleep stage classification in a subject with a determination system. The determination system comprises one or more sensors, one or more physical computer processors, and/or other components. The one or more physical computer processors are configured to execute computer program components. The computer program components comprise a respiratory activity component, a frequency component, a spectral boundary component, a sleep stage component, and/or other components. The operations of method 400 presented below are intended to be illustrative. In some embodiments, method 400 may be accomplished with one or more additional operations not described, and/or without one or more of the operations discussed. Additionally, the order in which the operations of method 400 are illustrated in FIG. 4 and described below is not intended to be limiting.

In some embodiments, method 400 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 400 in response to instructions stored electronically on an electronic storage medium. The one or more processing devices may include one or more devices configured through hardware, firmware, and/or software to be specifically designed for execution of one or more of the operations of method 400.

At an operation 402, output signals conveying information related to a respiratory wave amplitude metric are generated. In some embodiments, the respiratory wave amplitude metric is a power spectral density. In some embodiments, operation 402 is performed by one or more sensors the same as or similar to sensors 16 (shown in FIG. 1 and described herein).

At an operation 404, the information conveyed by the output signals in individual epochs of time is transformed into a frequency domain. In some embodiments, operation 404 is performed by a processor component the same as or similar to respiratory activity component 30 (shown in FIG. 1 and described herein).

At an operation 406, individual frequencies of respiratory wave amplitude metric peaks within the individual epochs of time are determined. In some embodiments, operation 406 is performed by a processor component the same as or similar to frequency component 32 (shown in FIG. 1 and described herein).

At an operation 408, an aggregated frequency of the respiratory wave amplitude metric peaks is determined by aggregating the individual frequencies of the respiratory wave metric peaks within the individual epochs of time. In some embodiments, determining the aggregated frequency of the respiratory wave amplitude metric peaks comprises averaging frequencies of power spectral density peaks from the individual epochs of time. In some embodiments, an average frequency of the power spectral density peaks from individual thirty second epochs of time during the sleep session is a mean respiratory frequency of the subject. In some embodiments, operation 408 is performed by a processor component the same as or similar to frequency component 32 (shown in FIG. 1 and described herein).

At an operation 410, spectral boundaries are determined. The spectral boundaries are determined based on the aggregated frequency. In some embodiments, the spectral boundaries are determined based on the mean respiratory frequency using linear regression. In some embodiments, operation 410 is performed by a processor component the same as or similar to spectral boundary component 34 (shown in FIG. 1 and described herein).

At an operation 412, sleep stages of the subject are determined. The sleep stages are determined during individual epochs of time in a subsequent sleep session as a function of the aggregated frequency of respiratory wave amplitude metric peaks using the determined spectral boundaries. In some embodiments, operation 412 is performed by a processor component the same as or similar to sleep stage component 36 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to determine subject specific spectral boundaries for sleep stage classification in a subject, the system comprising:
   one or more sensors configured to generate output signals that convey information related to a respiratory wave amplitude metric for a sleep session of the subject; and
   one or more physical computer processors configured by computer readable instructions to:
      transform the information conveyed by the output signals in a first set of individual epochs of time into a frequency domain;
      determine individual frequencies of respiratory wave amplitude metric peaks within the first set of individual epochs of time;
      determine an aggregated frequency of the respiratory wave amplitude metric peaks by aggregating the determined individual frequencies of the respiratory wave amplitude metric peaks;
      determine subject specific upper spectral boundaries and lower spectral boundaries for sleep stage classification for the subject based on the aggregated frequency, wherein the upper spectral boundaries are a function of the aggregated frequency and upper coefficients, and wherein the lower spectral boundaries are a function of the aggregated frequency and lower coefficients; and
      determine sleep stages of the subject during a second set of individual epochs of time in a subsequent sleep session as a function of the aggregated frequency of the respiratory wave amplitude metric peaks using the determined subject specific upper and lower boundaries.

2. The system of claim 1, wherein the one or more sensors and the one or more physical computer processors are configured such that the respiratory wave amplitude metric is a power spectral density.

3. The system of claim 2, wherein the one or more physical computer processors are configured such that determining the aggregated frequency of the respiratory wave amplitude metric peaks comprises averaging frequencies of power spectral density peaks from the first set of individual epochs of time.

4. The system of claim 3, wherein the one or more physical computer processors are configured such that an average frequency of the power spectral density peaks from individual thirty second epochs of time during the sleep session is a mean respiratory frequency of the subject.

5. The system of claim 4, wherein the one or more physical computer processors are configured such that the subject specific upper spectral boundaries are determined based on the mean respiratory frequency using linear regression and upper regression coefficients, and the lower spectral boundaries are determined based on the mean respiratory frequency using linear regression and lower regression coefficients.

6. A method to determine subject specific spectral boundaries for sleep stage classification in a subject with a determination system, the determination system comprising one or more sensors and one or more physical computer processors, the method comprising:
   generating, with the one or more sensors, output signals that convey information related to a respiratory wave amplitude metric for a sleep session of the subject;
   transforming, with the one or more physical computer processors, the information conveyed by the output signals in a first set of individual epochs of time into a frequency domain;
   determining, with the one or more physical computer processors, individual frequencies of respiratory wave amplitude metric peaks within the first set of individual epochs of time;
   determining, with the one or more physical computer processors, an aggregated frequency of the respiratory wave amplitude metric peaks by aggregating the individual frequencies of the respiratory wave amplitude metric peaks within the first set of individual epochs of time;
   determining, with the one or more physical computer processors, subject specific upper spectral boundaries and lower spectral boundaries for sleep stage classification for the subject based on the aggregated frequency, wherein the upper spectral boundaries are a function of the aggregated frequency and upper coefficients, and wherein the lower spectral boundaries are a function of the aggregated frequency and lower coefficients; and
   determining, with the one or more physical computer processors, sleep stages of the subject during a second set of individual epochs of time in a subsequent sleep session as a function of the aggregated frequency of the respiratory wave amplitude metric peaks using the determined subject specific upper and lower spectral boundaries.

7. The method of claim 6, wherein the respiratory wave amplitude metric is a power spectral density.

8. The method of claim 7, wherein determining the aggregated frequency of the respiratory wave amplitude metric peaks comprises averaging frequencies of power spectral density peaks from the first set of individual epochs of time.

9. The method of claim 8, wherein an average frequency of the power spectral density peaks from individual thirty second epochs of time during the sleep session is a mean respiratory frequency of the subject.

10. The method of claim 9, wherein the subject specific upper spectral boundaries are determined based on the mean respiratory frequency using linear regression and upper regression coefficients, and the lower spectral boundaries are determined based on the mean respiratory frequency using linear regression and lower regression coefficients.

* * * * *